United States Patent [19]

Fisher

[11] Patent Number: 4,917,774

[45] Date of Patent: * Apr. 17, 1990

[54] METHOD FOR ANALYZING ADDITIVE CONCENTRATION

[75] Inventor: Gordon Fisher, Sudbury, Mass.

[73] Assignee: Shipley Company Inc., Newton, Mass.

[*] Notice: The portion of the term of this patent subsequent to Apr. 17, 2007 has been disclaimed.

[21] Appl. No.: 855,360

[22] Filed: Apr. 24, 1986

[51] Int. Cl.$^4$ ............................................. G01N 27/46
[52] U.S. Cl. ................................. 204/153.1; 204/402; 204/434
[58] Field of Search ......................... 204/1 T, 434, 402

[56] References Cited

U.S. PATENT DOCUMENTS

| | | | |
|---|---|---|---|
| 4,132,605 | 1/1979 | Tench et al. | 204/1 T |
| 4,146,437 | 3/1979 | O'Keefe | 204/434 |
| 4,496,454 | 1/1985 | Berger | 204/402 |
| 4,566,949 | 1/1986 | Berger | 204/1 T |
| 4,595,462 | 6/1986 | Vangaever et al. | 204/1 T |
| 4,735,691 | 4/1988 | Green et al. | 204/402 |
| 4,786,373 | 11/1988 | Saloheimo et al. | 204/402 |

FOREIGN PATENT DOCUMENTS 1531761  11/1978  United Kingdom ................ 204/402

OTHER PUBLICATIONS

Dennis Tench et al., J. Electrochem. Soc., vol. 132, No. 4, pp. 831–834, Apr. 1985.
"Cyclic Pulse Voltammetric Stripping Analysis of Acid Copper", J. Electrochem Soc., Electrochemical Science and Technology, Apr., 1985, pp. 831–834.

Primary Examiner—T. Tung
Attorney, Agent, or Firm—Robert L. Goldberg

[57] ABSTRACT

A method for determining the effective quantity of an organic additive in an electroplating bath involving passing an inert electrode through a predetermined sequence of voltammetric steps including a step of plating the electrode at a given applied potential, stripping the plated metal at a given applied potential, and conditioning the inert electrode without applied potential; correlating the quantity of additive with the coulombs utilized during the metal stripping step; and using the same predetermined sequence of voltammetric steps for a bath having an unknown quantity of additive.

12 Claims, 2 Drawing Sheets

METHOD FOR ANALYZING ADDITIVE CONCENTRATION

BACKGROUND OF THE INVENTION

1. Field of the Invention

This invention relates to electrolytic plating and more particularly, to control of the additive content in an electroplating solution.

2. Description of the Prior Art

Electroplating is a complex process involving multiple ingredients in a plating bath. It is important that the concentration of several of the ingredients be kept within close tolerances in order to obtain a high quality deposit. In some cases, chemical analysis of individual solution constituents can be made regularly (such as pH measurement for acid content), and additions made as required. However, other addition agents such as brighteners, leveling agents, suppressants, etc. together with impurities cannot be individually analyzed on an economical or timely basis by a commercial plating shop. Their initial concentration is low and their quantitative analysis is complicated and subject to error.

A prior art method for controlling such ingredients in an electroplating bath is to make regular additions of particular ingredients based upon empirical rules established by experience. However, depletion of particular ingredients is not always constant with time or with bath used. Consequently, the concentration of the ingredient in the bath eventually diminishes or increases to a level where it is out of the range of acceptable tolerance. If the additive content does go out of range, the quality of the metal deposit suffers and the deposit may be dull in appearance and/or brittle or powdery in structure.

Another prior art method for plating bath control is to plate articles or samples and visually evaluate the plating quality to determine if the bath is performing satisfactorily. In standard Hull Cell and "Bone Pattern" tests, a specially shaped test specimen is plated and then evaluated to determine the quality of the deposit along the shape. This is a time consuming test which gives at best a rough approximation of the concentration of the constituents of the bath.

The electroplating of through-hole interconnections in the manufacture of multilayer printed circuit boards is an example of a use of an electroplated metal where high quality plating is required. It is known that the concentration of the addition agent within the plating solution must be maintained in low concentration (typically less than 100 parts per million parts of solution - ppm) in order to obtain acceptable deposits on printed circuit boards. This must be done to maintain proper mechanical properties for resistance to thermal stresses encountered during manufacture and use and to assure the proper thickness of the deposit in the through-holes. The concentration of the addition agent fluctuates because of oxidation at the anode, reduction and hydrogen retention at the cathode, and chemical degradation. When the additive level is insufficient, deposits are burnt and powdery in appearance whereas excessive addition agent induces brittleness and non-uniform deposition. Hull Cell tests, Bone Pattern Tests, and Pencil Tests, combined with periodic additions of fresh additive, were the methods used to maintain a controlled concentration of the additive until recently. These methods were unreliable and circuit board quality suffered as a consequence of these unreliable methods.

A more recent method for evaluating the quality of an electroplating bath was disclosed in U.S. Pat. No. 4,132,605 to Tench (hereafter the Tench patent) incorporated herein by reference. In accordance with the procedures of the Tench patent, the potential of a working electrode is swept through a voltammetric cycle, including a metal plating range and a metal stripping range, for at least two baths of known plating quality and an additional bath whose quality or concentration of additives is to be evaluated. The integrated or peak current utilized during the metal stripping range is correlated with the quality of the bath of known quality. The integrated or peak current utilized to strip the metal in the bath of unknown quality is compared to the correlation and its quality evaluated. In a preferred embodiment of said patent, the potential of an inert working electrode is swept by a function generator through the voltammetric cycle. A counter electrode immersed in the plating bath is coupled in series with a function generator and a coulometer to measure the charge from the working electrode during the stripping portion of the cycle.

An improvement to the method disclosed in said U.S. Pat. No. 4,132,605 is described by Tench and White, in the *J. Electrochem. Soc.*, Electrochemical Science and Technology, April, 1985, pp. 831-834, (hereafter the Tench publication) incorporated herein by reference. In accordance with the Tench publication, contaminant build up in the copper plating bath affects the copper deposition rate and thus interferes with additive analysis. The Tench publication teaches that rather than the continuous sweep cycle utilized in the above reference patent, a method be used involving sequentially pulsing the electrode between appropriate plating, stripping, cleaning, and equilibrium potentials whereby the electrode surface is maintained in a clean and reproducible state. Stated otherwise, where the process of the Tench patent involves a continuous voltammetric sweep between about $-600$ millivolts and $+1,000$ millivolts versus a working electrode and back over a period of about 1 minute, the Tench publication pulses the potential, for example at $-250$ mV for 2 seconds to plate, $+200$ mV for a time sufficient to strip, $+1,600$ mV to clean for seconds, $+425$ mV for 5 seconds to equilibrate, all potentials referenced to a saturated Calomel electrode, after which the cycle is repeated until the difference between successive results are within a predetermined value, for example, within 2% of one another.

The procedure of the Tench publication provides some improvement over the procedure of the Tench patent, but during continuous use of an electroplating bath and following successive analyses, contaminants build up on the electrodes and analysis sensitivity is lost.

SUMMARY OF THE INVENTION

The subject invention is an improvement over the processes described both in the Tench patent and the Tench publication. In accordance with the invention, using either the sweep method of the Tench patent, the pulse method of the Tench publication, or an adaptation of the pulse method, the build up of contaminants on an electrode surface is eliminated by a pause without applied potential following each completed cycle. This is effectuated by an open circuit condition, or an applied potential equal to or approximately the open circuit potential of the inert electrode in the bath following the cycle of plating, stripping, and if a pulsed system is used, cleaning. An applied potential equal to or approximately the open circuit potential can be applied in lieu of an equilibration step, or an open circuit condition can be used following equilibration. During either this applied potential or the open circuit condition, for reasons not fully understood, contaminants are either eliminated from the electrode surface or fail to deposit on the surface. Regardless of the mechanism, it has been found that to the sensitivity of the process using either an applied potential equal to or near the open circuit potential or the open circuit pause after a completed cycle is significantly improved.

DESCRIPTION OF THE PREFERRED EMBODIMENTS

The invention disclosed herein may be used with either the cyclic voltammetric stripping (CVS) method disclosed in the Tench patent, the cyclic pulse voltammetric stripping method (CPVS) disclosed in the Tench publication or an adaptation of the CPVS method. The preferred embodiment of the invention involves the CPVS method disclosed in the Tench publication and an open circuit condition following equilibration as this method provides greater sensitivity to additive concentration.

Regardless of whether the invention is applied to the CVS method or the CPVS method, the equipment used to perform the process is essentially the same as that disclosed in the Tench patent.

In general, using the process of this invention, a small amount of metal is electrodeposited onto an inert electrode such as platinum or gold under controlled conditions of electrode potential and mass transport in the solution. The amount of metal deposited is determined by integrating the current passed during redissolution or "stripping" of the deposited metal from the surface as the electrode potential proceeds through a cycle including plating and stripping. The quantity of metal deposited, and subsequently redissolved, is related to the concentration of additives affecting the rate of deposition. The cathodic current required to deposit the metal is also an indication of the deposition rate, but is less precise because of other possible reduction reactions, such as the reduction of hydrogen and organic compounds in the bath, occurring during the cathodic portion of the cycle.

Figure 1:
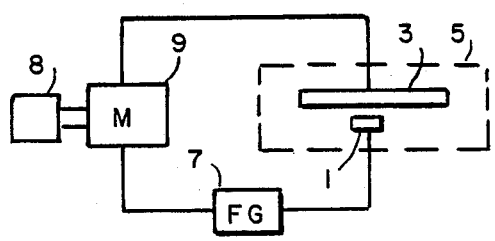
FIG. 1 is a schematic wiring diagram showing a device for practicing the method of the present invention.

FIG. 1 is a schematic wiring diagram showing a device for practicing the method of the present invention. A working electrode 1 and a counter electrode 3 are immersed in a bath in cell 5. The counter electrode is selected and designed so as not to be easily polarized in the particular bath being evaluated. This is accomplished in part, by making the counter electrode large relative to the working electrode and by placing it close to the working electrode.

A generator 7 either sweeps the working electrode 1 through a potential vs. time cycle at a specific predetermined rate or pulses the working electrode 1 through fixed potentials during a timed cycle, dependent upon whether the CVS or CPVS method is employed. A coulomb meter 9 measures the coulombs, (amps-seconds) flowing between the counter electrode 3 and the working electrode 1 during the metal stripping portion of the voltammetric cycle. The coulometer may be an ammeter whose output can be fed into an x-y recorder for determining the coulombs utilized during the stripping portion of the cycle, or the output can go directly into a microprocessor or minicomputer 8 for direct correlation and comparison of the coulombs utilized.

Figure 2:
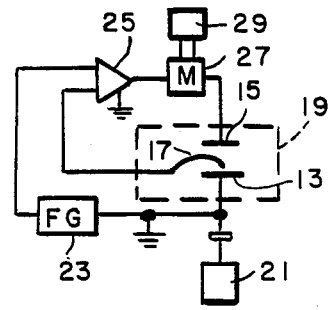
FIG. 2 is a schematic wiring diagram for an alternative device for practicing the method of the present invention.

FIG. 2 shows a schematic wiring diagram for a more elaborate device for practicing the invention. Three electrodes, a working electrode 13, a counter-electrode 15, and a reference electrode 17, are immersed in a bath cell 19. To establish relative motion between the working electrode 13 and the bath, a motor 21 is used to rotate the working electrode 13 to which contact is made by slip brushes.

In one embodiment of the invention, the working electrode 13 is platinum and the counter-electrode 15 is a platinum - 10% rhodium alloy, although any conductive material, such as gold, can be used. The rotatable working electrode 13 has a flat, polished surface, 0.13 cm$^2$ in area, mounted flush with the end of a 1.27 cm diameter Kel-F cylinder. The reference electrode 17 is conveniently, a saturated calomel reference electrode (SCE).

A function generator 23 and an electronic potentiostat 25 are used to control the potential of the working electrode relative to the reference electrode 17. A digital coulometer 27 measures the coulombs flowing during the stripping portion of the voltammetric cycle. For laboratory testing of the method, instrumentation such as a Princeton Applied Research (PAR) model 273 galvanostat potentiostat under computer control (Apple IIe) may be used. Using a suitable program, the potential - time sequence above is applied to the working electrode, the stripping current digitized and integrated as a function of time to obtain the number of coulombs passed which is then displayed for each analysis cycle. The output of the device can also be plotted on an x-y recorder to graphically display the voltammetric cycle or stripping current versus time.

A microprocessor or minicomputer 29 can be coupled to the digital coulometer to compare the measured coulombs with a previously established correlation. The microprocessor or minicomputer 8, 29, shown in FIGS. 1 and 2, can be coupled to the circuit so that they are triggered either manually or by a suitable signal from the function generator 7, 23, or from the working electrode 1, 13. Instrumentation to accomplish these functions is available commercially from UPA Technology Inc. of Syossett, N.Y. under the tradename Qualiderm Q-1000A.

The preferred method of the invention applies a pause or open circuit condition (no applied potential) following each CPVS cycle. This can be schematically illustrated as follows:

$$V_{plate} \text{-} V_{strip} \text{-} V_{clean} \text{-} V_{equilibrate} \text{-} V_{open}$$

With respect to potential and time parameters for the steps of plating, stripping, cleaning and equilibrating, these parameters are essentially in accordance with the teachings of the Tench publication above. Plating is conducted at a negative potential, such as from $-100$ to $-500$ mV, preferably at approximately $-250$ mV for 2 seconds, stripping at a positive potential, preferably at least $+100$ to 600 mV, more preferably at approximately $+200$ mV for the time necessary to strip all copper from the electrode, cleaning at a high positive potential, generally in excess of $+1,000$ mV, preferably at approximately $+1,600$ mV for about 5 seconds, and equilibration at a relatively high positive potential, generally from $+200$ to $+750$ mV, preferably at approximately $+425$ mV for seconds. After the CPVS cycle, the circuit is left open (no applied potential) preferably for at least 5 seconds, and more preferably, for a period of time varying between 10 and 30 seconds. During this period of time, there will be a potential reading of about $+600$ mV due to what is believed to be an oxidation - reduction reaction taking place at the electrode surface.

In an alternative lesser preferred embodiment of the invention, the open circuit condition can be combined with the equilibration step in which case, an applied potential equal to or near that of the oxidation - reduction reaction that exists during open circuit of from about $+600$ to $+700$ mV is used for about 5 to 30 seconds instead of the equilibration step and the open circuit condition is omitted. This procedure provides improvement over the procedure of either the Tench patent or publication but is less sensitive than the procedure utilizing an open circuit condition following equilibration in the CPVS method.

To achieve maximum sensitivity using the process of this invention, there must be sufficient relative motion between the working electrode and the bath to maintain a uniform supply of plating ingredients at the electrode surface. Without such motion, the bath becomes depleted at the surface and the deposition rate obtained does not reflect the correct rate for the bulk solution. In the embodiment shown in FIG. 2, the working electrode 13 is rotated by motor 21 to obtain controlled relative motion between it and the plating bath. Other means for obtaining relative motion can be used, such as a pump for moving the bath across the face of the electrode.

EXAMPLE 1

A potential - time diagram can be formulated in accordance with the procedures of this invention utilizing a copper plating bath of the following composition:

| | | |
|---|---|---|
| Copper Sulfate Pentahydrate | 110 | gms |
| Sulfuric Acid (1.84 S.G.) | 212 | gms |
| Chloride Ion as HCl | 70 | ppm |
| Additive Electroposit 892 | 5 | ml |
| Water | | to 1 liter |

The above bath is used at a temperature of 2.6° C. The CPVS process with an open circuit pause was used for purposes of this example.

The organic additive used is a proprietary additive sold under the tradename Electroposit ®892 and is available from Shipley Company Inc., of Newton, Mass.

Figure 3:
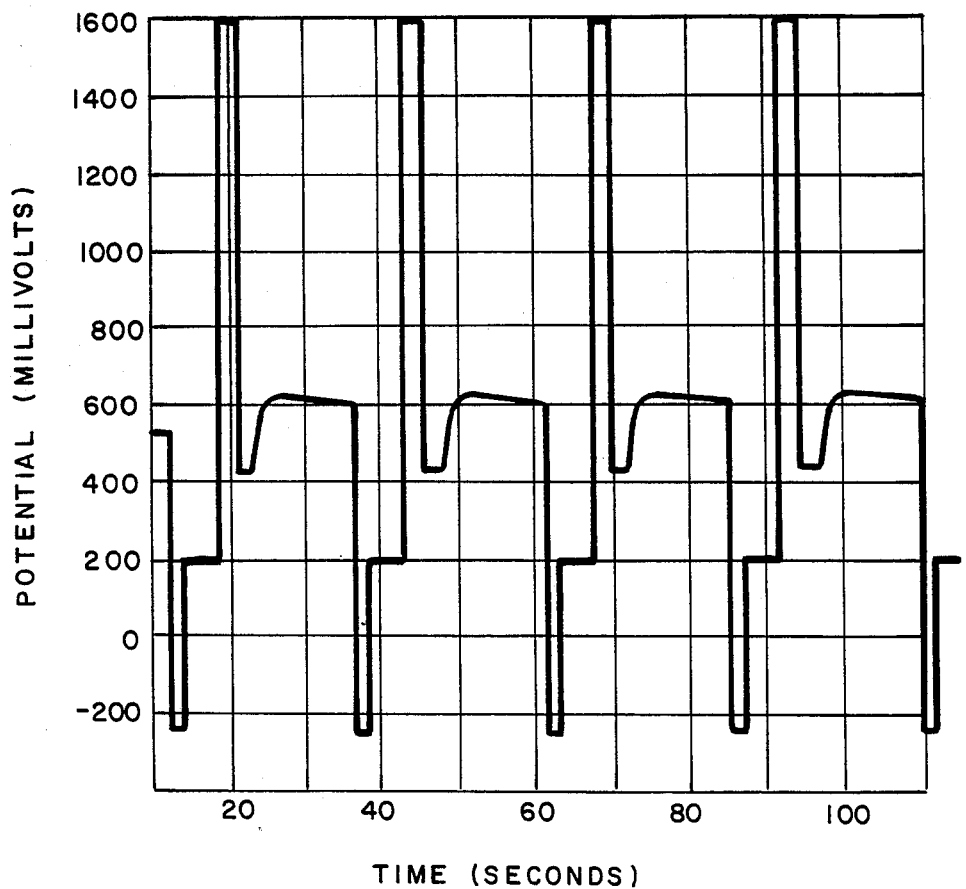
FIG. 3 is a potential - time diagram representing a CPVS cycle with an open circuit step inserted in the sequence in accordance with the invention.

FIG. 3 of the drawings is a potential time diagram representing a CPVS cycle with an open circuit step obtained using the above formulation. Four cycles are shown beginning with start up through completion of the 4th cycle to obtain equilibrium conditions. The initial applied potential is set at $-250$ mV for 2 seconds to plate copper onto the electrode. After plating for 2 seconds, the applied potential is increased to $+200$ mV to strip plated copper from the electrode. Approximately 6 seconds are required to strip all of the copper from the electrode. The applied potential is then increased to $+1,600$ mV to clean the electrode and is held at this potential for 4 seconds. For equilibration, the applied potential is reduced to $+425$ mV for 5 seconds. Following equilibration, in accordance with the procedures of this invention, the circuit is left open with no applied potential for approximately 20 seconds. During this period of time, the potential rapidly increases to in excess of $+600$ mV and then gradually declines to approximately $+600$ mV. The positive potential reading without applied potential is due to an oxidation - reduction reaction established on the inert electrode as it is immersed in the bath solution in an open circuit condition.

The above procedure is repeated through additional cycles until the difference between successive values of the integrated stripping current are within a predetermined value which was 2% for purposes of this example.

Figure 4:
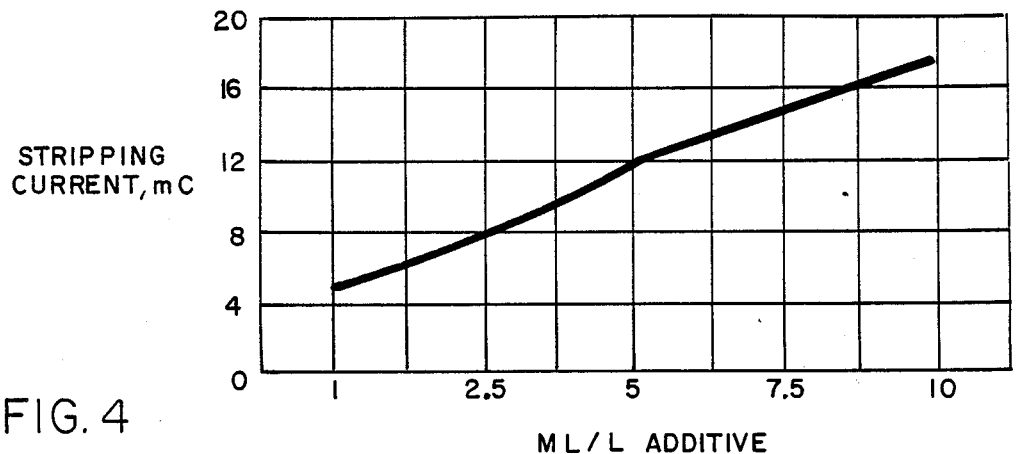
FIG. 4 correlates concentration of additive with coulombs and is derived from FIG. 3.

In the bath utilized for FIG. 3, the concentration of the organic additive was 5 ml/liter. The procedure is repeated until a series of curves are generated for baths with differing additive concentrations. From this data, a graph showing concentration as a function of integrated stripping current (expressed in millicoulombs) is generated. The graph generated for the above formulation is represented in FIG. 4 of the drawings.

EXAMPLE 2

Figure 5:
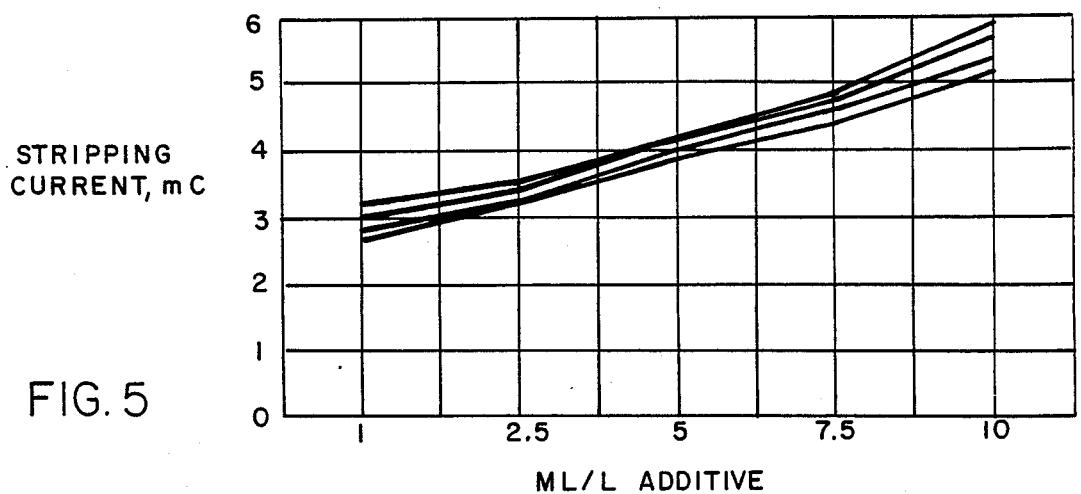
FIG. 5 correlates concentration of additive with coulombs and is generated from a potential - time diagram (not shown) using a CPVS cycle omitting the open circuit step in the sequence of steps.

The procedure of Example 1 was repeated but the open circuit condition was omitted. The results are graphically displayed in FIG. 5 of the drawings. A comparison of FIGS. 4 and 5 shows a significantly steeper slope for the curve of FIG. 4 relative to FIG. 5 thereby establishing that the procedure of Example 1 is significantly more sensitive than the procedure of Example 2.

According to the method of the invention, potential - time cycles are run under controlled conditions of electrode potential and mass transport in the solution for baths of known quality, or of known concentration of additives, to obtain the total coulombs passed during the stripping step of the cycle. The quality or concentration is then correlated with the coulombs passed during stripping to obtain the concentration as a function of the stripping coulombs.

In some cases, some variation in the stripping current is observed from day to day for a particular bath composition and are probably caused by uncontrolled variables, such as changes in the working electrode surface and operating temperature. Such variations can be mitigated by measuring the stripping current utilized by a fixed standard immediately before or after making the desired measurement and then utilizing the ratio of the two measurements to obtain the correlation between stripping current and concentration of ingredients. In addition, controlling the operating temperature of the bath within 1° C. will greatly reduce these variations.

As aforesaid, FIG. 4 shows a correlation of stripping coulombs as a function of the effective concentration of the brightener for the electrode plating bath. The correlation need not be for an absolute quantity of leveling agent. For example, the correlation can be for a particular quality level as shown by $Q_1$ and $Q_2$ in FIG. 6. The distance between $Q_1$ and $Q_2$ represents a bath of acceptable quality for a particular type defect between two quality extremes, $Q_1$ and $Q_2$. The regions outside of the area encompassed by $Q_1$ and $Q_2$ represent deposits of unacceptable quality. Separate external standards could be used to obtain the ratio. In some cases, sufficient accuracy could be obtained by plotting stripping coulombs directly.

Figure 6:
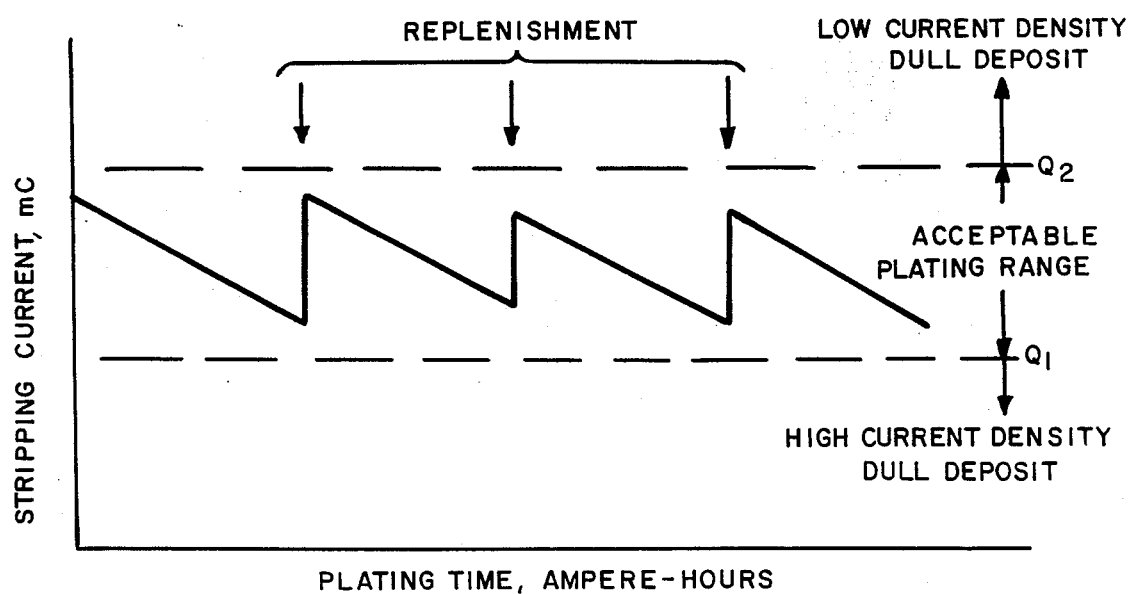
FIG. 6 represents an alternative method for determining additive concentration based upon deposit quality.

The correlations shown in FIGS. 4 or 6 are used to determine the quality or concentration of additive agent in an unknown bath. A similar ratio or stripping coulombs is determined for the unknown bath and then compared to the correlations in FIGS. 4 or 6 to obtain the corresponding quality or concentration. Since the method is based upon comparison, the standards used to obtain the correlation should be representative of the conditions of the unknown bath, or any variations between the baths should be accounted for. Similarly, the unknown baths should be operated under similar conditions of electrode potential and mass transport (temperature, atmosphere, agitation, etc.) as for the standards, or any variations in operation should be accounted for.

Although there is a wide variety of plating baths for various plating metals, including copper, nickel, chromium, zinc, tin, lead, gold, silver, and cadmium, the same principles are involved in their application. Additives are used in copper plating baths and peptone is commonly used in tin or tin/lead fluoroborate plating baths to affect the metal deposition rate. Thus, the present invention is applicable for evaluating the quality or concentration of additives which affect the plating rate in all such plating baths and all additives or variables which have an effect on plating rate.

I claim:

1. A method for determining the effective quantity of organic additive in an electroplating bath comprising the steps of:
    a. obtaining a plurality of plating baths, each having a known and different quantity of organic additive;
    b. for each bath, repeatedly cycling an inert electrode through a predetermined sequence of voltammetric steps where for each cycle, a first step is within a metal plating range, a next step is within a metal stripping range, a next step of cleaning the inert electrode and a final step is without applied potential whereby the electrode is prepared for the next subsequent cycle initiated upon completion of the prior cycle;
    c. correlating the effective quantity of additive with the coulombs utilized during the metal stripping step;
    d. obtaining a plating bath having an unknown quantity of organic additive, repeatedly cycling a working electrode through said bath using the aforesaid predetermined sequence of voltammetric steps until a steady state condition is obtained for said bath;
    e. measuring the coulombs utilized during the metal stripping step of said cycle for said bath having an unknown quantity of organic additive; and
    f. choosing from said correlation a quantity of organic additive which corresponds to said coulombs utilized for said bath with said unknown quantity of organic additive.

2. The method of claim 1 where the voltammetric step without an applied potential is for a period of at least five seconds.

3. The method of claim 2 where the working electrode is continuously swept through said sequence of voltammetric steps.

4. The method of claim 2 where the working electrode is cycled through said series of voltammetric steps at a constant potential for each of said steps.

5. The method of claim 2 where the sequence of voltammetric steps includes the step of equilibrating the inert electrode.

6. The method of claim 2 where the voltammetric step without an applied potential for a period of from 20 to 30 seconds.

7. The method of claim 2 where the electroplating bath comprises a bath for electroplating copper.

8. The method of claim 1 where the predetermined sequence of voltammetric steps includes the step of equilibrating the inert electrode, each step being at a constant applied potential.

9. A method for determining the effective quantity of organic leveling agent in a copper electroplating bath comprising the steps of:
    a. obtaining a plurality of plating baths, each having a known and different quantity of organic leveling agent;
    b. for each bath, repeatedly cycling an inert electrode through a predetermined sequence of voltammetric steps at constant potential for each step where for each cycle a first voltammetric step is within a metal plating range, a next step is within a metal stripping range, a next step is cleaning the inert electrode, and a final step is without applied potential whereby the electrode is prepared for the next subsequent cycle initiated upon completion of the prior cycle;
    c. correlating the effective quantity of organic leveling agent with the coulombs utilized during the metal stripping step;
    d. obtaining a bath having an unknown quantity of organic leveling agent, repeatedly cycling a working electrode through said bath using the aforesaid predetermined sequence of voltammetric steps until a steady-state condition is obtained for said bath;
    e. measuring the coulombs utilized during said metal stripping step of said cycle for said bath having a unknown quantity of leveling agent; and
    f. choosing from said correlation a quantity of organic leveling agent which corresponds to said coulombs utilized for said bath having an unknown quantity of organic leveling agent.

10. The method of claim 9 where the voltammetric step without an applied potential is for a period of at least five seconds.

11. The method of claim 10 where the sequence of voltammetric steps includes the step of equilibrating the inert electrode.

12. The method of claim 10 where the voltammetric step without an applied potential is for a period of from 20 to 30 seconds.

* * * * *